United States Patent [19]

Steer

[11] Patent Number: 4,925,216
[45] Date of Patent: May 15, 1990

[54] METHOD AND APPARATUS FOR ATTACHING A CATHETER TO A BAG SUCH AS A WOUND DRAINAGE BAG

[75] Inventor: Peter L. Steer, Surrey, England

[73] Assignee: E. R. Squibb and Sons, Inc., Princeton, N.J.

[21] Appl. No.: 175,977

[22] Filed: Mar. 31, 1988

[30] Foreign Application Priority Data

Apr. 9, 1987 [GB] United Kingdom ............ 8708493
Apr. 24, 1987 [GB] United Kingdom ............ 8709816

[51] Int. Cl.⁵ ........................................... F16L 55/00
[52] U.S. Cl. ................................. 285/3; 285/200; 604/277; 604/334
[58] Field of Search ............... 285/200, 3; 604/277, 604/333, 334

[56] References Cited

U.S. PATENT DOCUMENTS

| Re. 29,139 | 7/1977 | Nordby et al. | 128/275 |
|---|---|---|---|
| 1,933,117 | 10/1933 | Markle | 285/3 |
| 2,902,036 | 9/1959 | Perry | 128/283 |
| 3,216,420 | 11/1965 | Smith et al. | 128/283 |
| 3,285,627 | 11/1966 | Kozulla et al. | 285/3 |
| 3,292,625 | 12/1966 | Marsan | 128/283 |
| 3,391,951 | 7/1968 | Miller | 285/3 |
| 3,830,235 | 8/1974 | Marsan | 128/227 |
| 3,910,274 | 10/1975 | Nolan | 128/227 |
| 3,983,446 | 7/1975 | Miller | 128/2 A |
| 4,017,020 | 4/1977 | Frank | 229/62 |
| 4,022,205 | 5/1977 | Tenczar | 285/3 X |
| 4,050,461 | 9/1977 | Ruby | 128/227 |
| 4,084,590 | 4/1978 | Caraway et al. | 128/283 |
| 4,203,445 | 5/1980 | Jessup et al. | 128/283 |
| 4,213,458 | 7/1980 | Nolan et al. | 128/283 |
| 4,268,286 | 5/1981 | Steer et al. | 55/278 |
| 4,519,793 | 5/1985 | Galindo | |
| 4,530,525 | 7/1985 | Schneider | 285/200 |
| 4,553,967 | 11/1985 | Ferguson et al. | 604/317 |
| 4,589,185 | 5/1986 | Schneider | 29/432 |

FOREIGN PATENT DOCUMENTS

| 54039 | 4/1980 | Australia . |
| 468148 | 9/1950 | Canada . |
| 962664 | 7/1964 | United Kingdom . |
| 2135652 | 9/1984 | United Kingdom . |

*Primary Examiner*—Thomas F. Callaghan
*Attorney, Agent, or Firm*—Donald J. Barrack; Robert E. Lee, Jr.

[57] ABSTRACT

Apparatus for attaching a catheter to a bag includes a pair of coupling rings for trapping a part of the bag wall between them. A cutter having a blade of circular or closed loop form makes a cut in the trapped wall and an elastomeric member for gripping a catheter is connectable to the cutter or to one of the rings. The catheter is inserted in the elastomeric member and through the rings, the member serving as a gaiter.

9 Claims, 4 Drawing Sheets

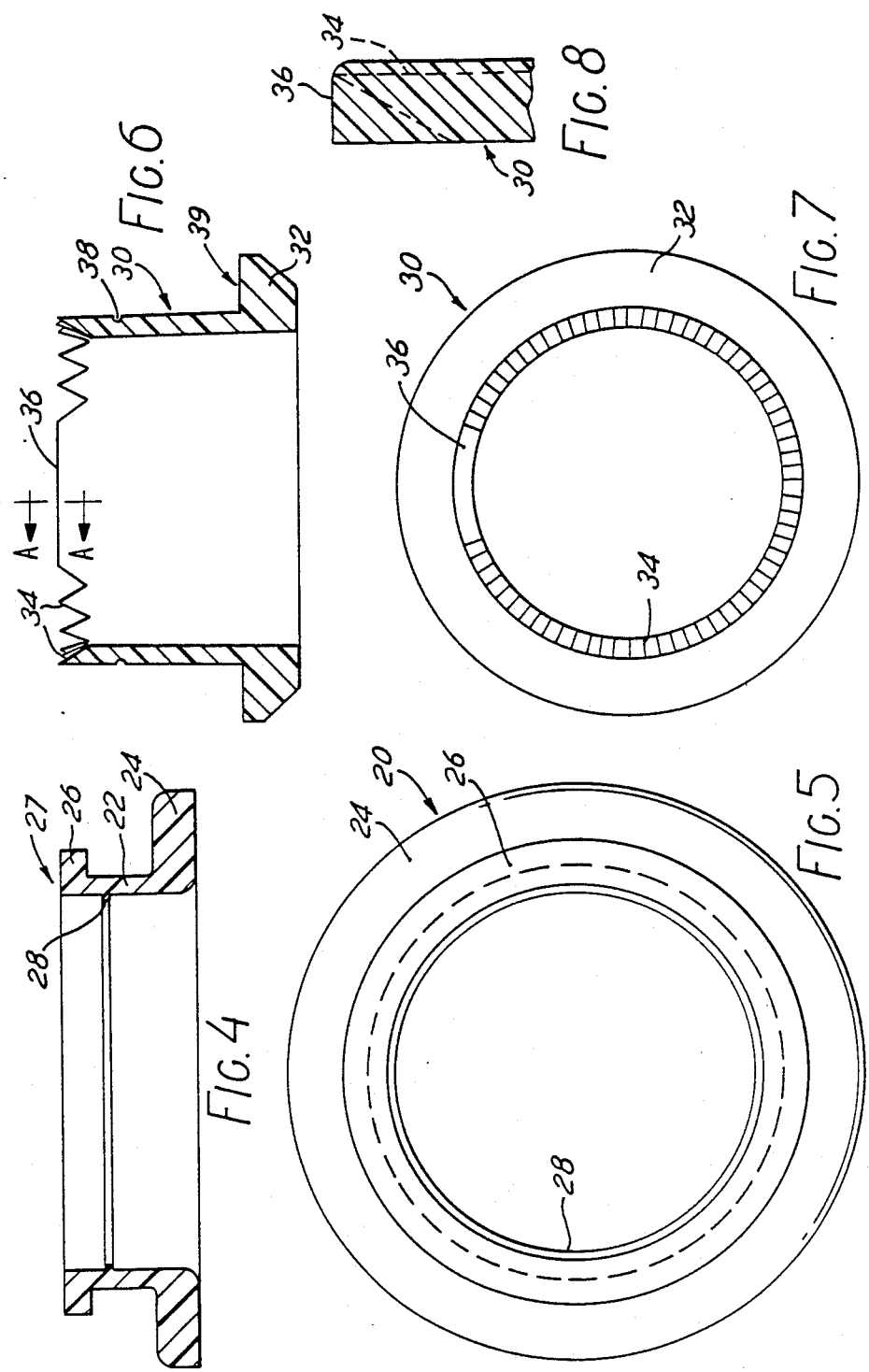

METHOD AND APPARATUS FOR ATTACHING A CATHETER TO A BAG SUCH AS A WOUND DRAINAGE BAG

BACKGROUND OF THE INVENTION

Schneider in U.S. Pat. Nos. 4,530,525 and 4,589,185 disclose a device and method for use in forming an access port, and also in forming a leakproof seal between a catheter tube and the film wall of an ostomy or wound cover pouch.

SUMMARY OF THE INVENTION

According to an aspect of the present invention, there is provided a method of attaching a catheter to a bag which receives discharge from a patient which includes trapping a portion of the bag wall between internal and external coupling rings so as to form a stretched area of bag wall within the rings, pushing a cutter blade of hollow tubular form into the external coupling ring and through the bag wall, the cutter blade having attached thereto or forming part thereof an elastomeric catheter gripping member of substantially conical shape, and then continuing to push the hollow blade into the internal coupling ring so that a peripheral detent on either the exterior of the blade or the interior of the internal coupling ring engages with a counterpart groove or channel on the interior of the internal coupling ring or the exterior of the hollow cylindrical blade as the case may be.

In this way, the parts may be held securely together and the catheter may be held in position by the elastomeric gripping member.

In a preferred form of the invention, the blade has serrated teeth around a predominant part, but not the whole periphery, of its cutting edge. This arrangement enables one to ensure that a disc of bag wall material is not entirely cut free from the bag wall, but, rather, remains attached thereto by virtue of the uncut portion.

The elastomeric member, which serves in use as a catheter "gaiter", may be of stepped form, decreasing in diameter in a direction away from the cutter blade. Hence, catheters of different outside diameters can be gripped by a single gaiter.

Also in accordance with the invention, apparatus for attaching a catheter to a bag includes a first (herein also called internal) coupling ring having a radially extending flange, a second (herein also called external) coupling ring also having a radially extending flange, the second ring having a diameter such that it snugly surrounds the unflanged part of the first ring, and a hollow substantially cylindrical cutter blade having a diameter less than the internal diameter of the second ring, the cutter blade being integral with or carrying an elastomeric member which is capable of gripping a catheter.

The words "internal" and "external" when applied to coupling rings in this specification are used in the sense of internal and external to the bag, as the case may be.

The manner of use of such apparatus will be understood from the foregoing paragraph describing a method in accordance with the invention.

BRIEF DESCRIPTION OF THE DRAWINGS

FIGS. 4 and 5 are respectively axial cross-sectional view and elevation of an external coupling ring for use in the invention;

FIGS. 6 and 7 are respectively axial cross-section and elevation, looking in the direction of the axis, one of example of cutter blade useful in the present invention;

FIG. 8 is a diagrammatic scrap cross-section on an enlarged scale on the line A—A of FIG. 6, illustrating an area of the cutter blade where no teeth are provided.

DETAILED DESCRIPTION OF THE INVENTION

This invention relates to a method and apparatus for attaching a catheter to a bag such as a wound drainage bag.

It would be desirable if there was a method and apparatus including a minimum number of parts and which can be easily manipulated. The present invention aims to meet this need.

According to the present invention, there is provided a method of providing access for a catheter to the interior of a bag which receives discharge from a patient which includes trapping a bag wall between internal and external coupling rings so as to form a stretched area of bag wall within the rings, and then pushing a cutter blade of circular form through the said stretched area.

Also according to the invention, there is provided apparatus for attaching a catheter to a bag including a pair of coupling rings for trapping a part of the bag wall between them, a cutter having a blade of circular or closed loop form for making a cut in said part, and an elastomeric member for gripping a catheter which is connectable to the cutter or to one of the pair of coupling rings.

Figure 2:
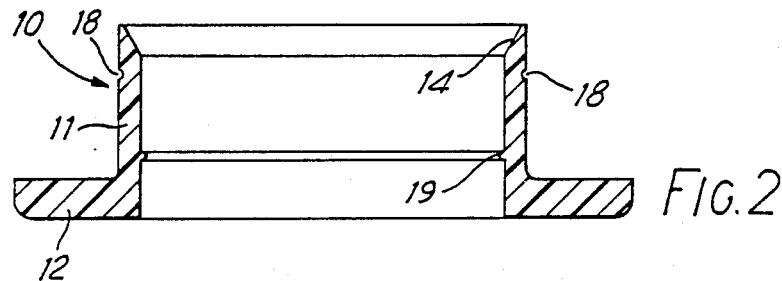
FIGS. 2 and 3 are respectively an axial cross-section and a front elevation of one example of internal coupling ring for use in the invention.
Figure 3:
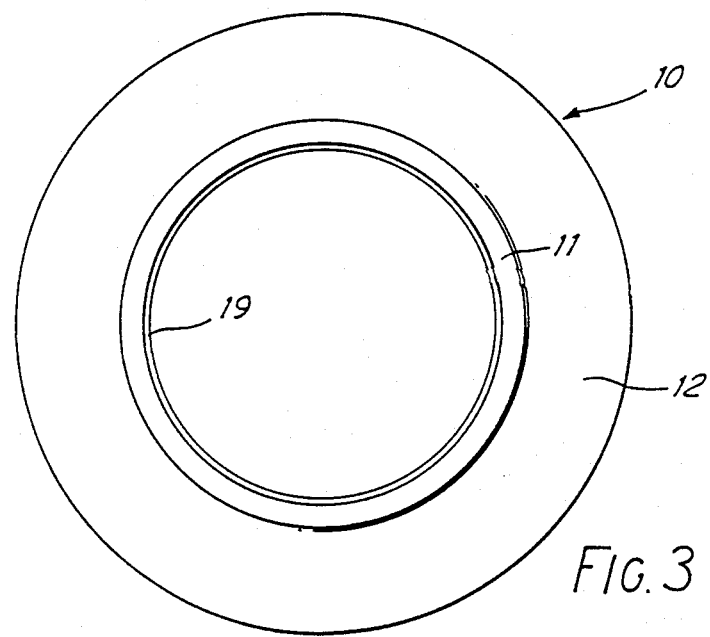

Referring firstly to FIGS. 2 and 3, the illustrated internal coupling ring comprises a hollow cylindrical body portion 11 and a laterally extending flange 12. The end of the cylindrical body portion 11 further from the flange 12 is chamfered as seen at 14. An external groove or channel 18 is located in the outer surface of the body portion 11. This is semi-circular cross section but other shapes could be employed. An internally projecting encircling rib 19 is provided on the inner wall surface of the body portion 11.

The external coupling ring 20 includes a substantially cylindrical body portion 22, a laterally extending flange 24, and a second laterally extending flange 26 on the opposite end of the body portion from the first flange. On the interior wall surface of the body portion there is provided an inwardly extending encircling bump or rib 28. As illustrated, this is semi-circular in cross section but other shapes could be employed. The function of the rib 28 is to engage in the counterpart groove or channel 18 on the internal coupling ring, when the external coupling ring 20 is placed over the ring 10.

Referring now to FIGS. 5 and 6 these show a cutter blade of hollow tubular shape having serrated teeth 34 around a major part of the periphery of one end of the hollow blade 30. This blade 30 has a relatively thick radially extending flange 32 at one end and the teeth 34 are provided at the other end. No teeth are provided over a limited peripheral portion 36. The portion 36 may have an angular extent of from 20 to 60 degrees, and preferably subtends about 40°. In the preferred version of the invention, the body portion tapers slightly from the larger diameter at its end corresponding to the flange 32 to a lesser diameter at its end corresponding to the teeth 34. The outside diameter of this end portion may for example be from 0.2% to 0.3% less than the outside diameter of the body portion immediately adjacent to the flange 32. In a particular preferred example, the relative difference in diameter may be 0.26%.

On the external surface of the body portion 30, there is provided a peripheral groove or channel 38 which, in the assembled position of the three illustrated parts, is engaged by the internally extending circular rib 19 on the internal coupling ring.

The components 10, 20 and 30 are plastic preferably made from an ABS resin (acrylonitrile-butadiene-styrene). That sold by Borg Warner under the Trade Name CYCOLAC is one material which is suitable.

The gaiter 40 is preferably made of a liquid silicone rubber or a thermoplastic elastomer. Its wall thickness may be from 0.020 to 0.030 inches, i.e. 0.51 to 0.75 millimeters.

Figure 9:
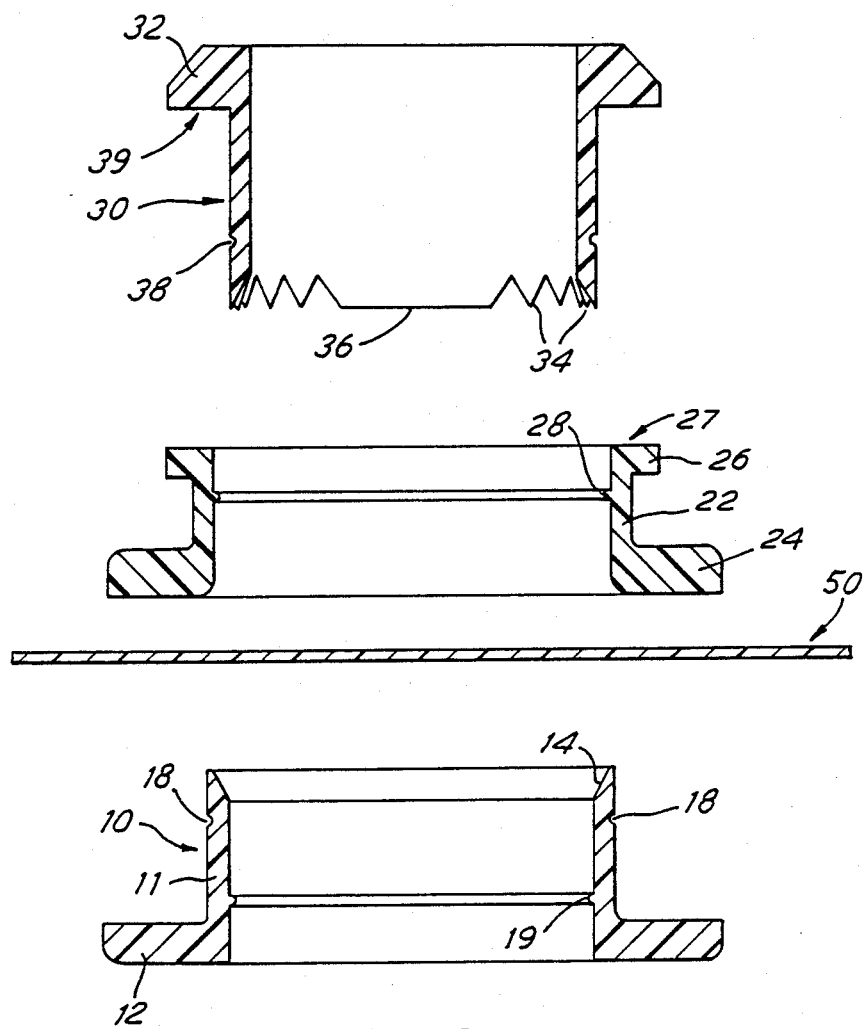
FIG. 9 is an exploded cross-section showing the internal and external coupling rings as they are about to grip the film wall of a pouch and showing how the cutter blade would then be pushed down through the external ring.
Figure 10:
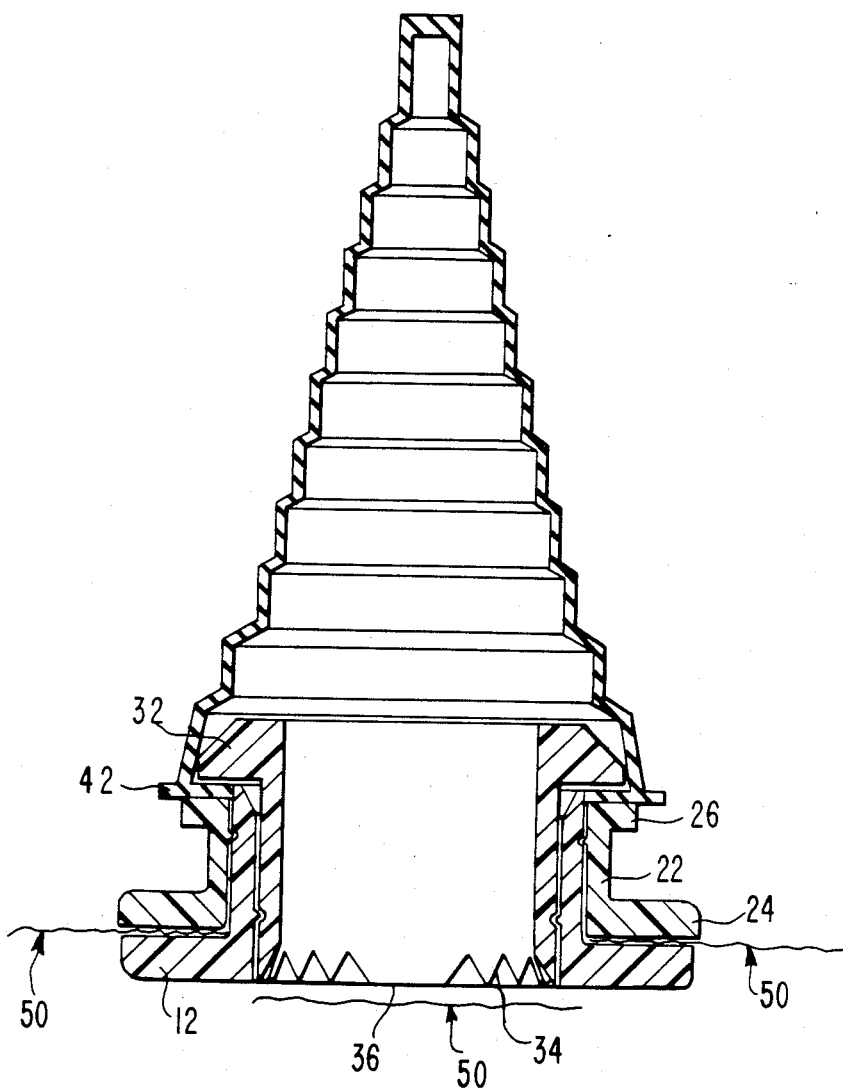

In operation, that is to say, in the assembly of the illustrated parts to connect a catheter (to be held by the gaiter 40) to a drainage bag or an ostomy bag, as shown in FIG. 9, the internal coupling ring is placed on the inside of a bag and the bag is arranged so that one of its walls 50 extends over the open end 14 of the internal ring 10. The external ring 20 is then slid over the internal ring so that an annular part of the bag wall 50 is clampled between the lower surface of flange 24 and the upper surface of flange 12, and another part of the bag wall 50, within said annular part, is stretched in a "drumhead" manner over the end 14. In the stretched condition of the bag wall and the fully pushed home position of the external coupling ring 20, the rib 28 engages in the channel 18 holding these parts together. Next the cutter blade 30 is presented with its toothed edge 34 towards the bag wall 50 stretched in drumhead fashion and is pushed down through the bag wall. In doing this the teeth 34 cut almost a complete circle and the cut away portion of the bag wall remains attached to the rest of the bag wall by virtue of the connection still existing because there are no teeth at the region 36. In this way, one can avoid producing a loose ring of cut out plastics material. The cutter blade 30 is then pushed home until the rib 19 springs into channel 38 due to the inherent resilience of the plastics material employed for the components 10, 20 and 30. Hence the cutter blade portion is connected to the coupling ring 10. The connection is a firm one, but is manually releasable. At this time, the surface 27 on the ring 20 and 39 on the blade 30 are slightly spaced apart.

Figure 1:
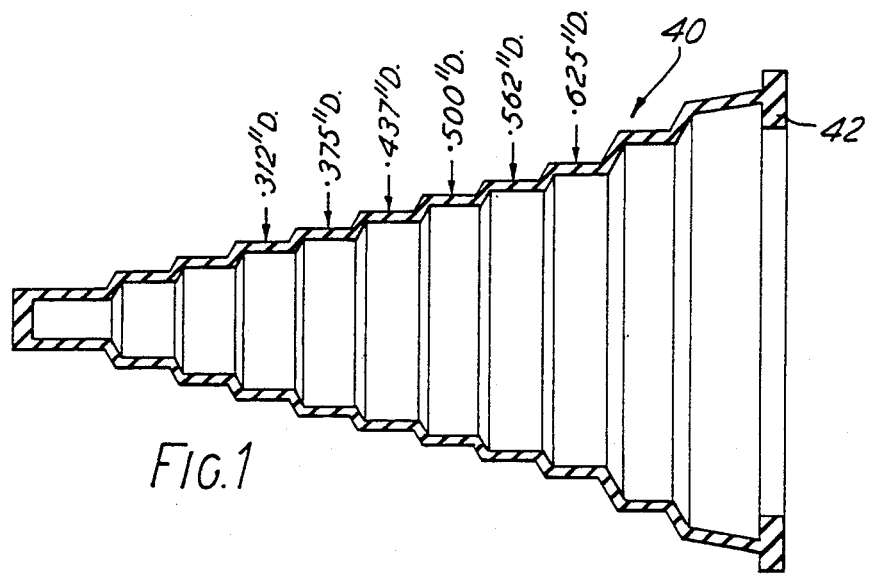
FIG. 1 illustrates a gaiter of elastomeric material of substantially part-conical shape for embracing a catheter to be held in position, shown in axial cross-section.

As the next stage in the operation of assembling the present device to attach a catheter, the elastomeric part conical gaiter or catheter holder member 40 is cut, e.g., with scissors, at a suitable position to receive a catheter of the size being used. As can be seen from the numerals on FIG. 1, the illustrated elastomeric part conical member can accommodate catheters of 0.312 inch diameter up to 0.625 inch diameter, making snug engagement with the external wall of the catheter and (due to the stretchy nature of the member 40) gripping the catheter against undesired movement. The larger end of the elastomeric member has an inwardly directed flange 42 which is lodged behind the surface 39 on flange 32 of cutter blade 30, to hold the gaiter onto the blade portion and hence onto the coupling rings 10 and 20. If desired, the catheter holder 40 can be assembled onto blade member 30 prior to the cutting operation.

As will be realized by a man of average skill in the art, other methods of making the various component parts of the present device captive to each other could be employed, without departing from the broad concept of the present invention which involves stretching a bag wall in "drumhead" fashion and then employing an axially movable closed loop cutter blade to provide the necessary orifice. In the preferred version of the invention, this cut is effected without entirely detaching the bag wall material within the defined cut.

The reference numerals or letters may be placed on the "steps" of the elastomeric member 40 so as to assist the user in judging where to make the cut appropriate to the particular outside diameter catheter.

While the cutter blade and the elastomeric gaiter have been described as separate parts, they could alternatively be integral or permanently secured together.

It is preferred that the components 10, 20 and 30 are each colored a different color by including a suitable dye in the plastics material. This assists a user in following written directions on how to assemble the device for use.

What is claimed is:

1. Apparatus for attaching a catheter to a bag comprising a pair of coupling rings for trapping a part of the bag wall between them, a cutter member having a blade of circular or closed loop form for making a cut in said part, and an elastomeric member for gripping a catheter which is connectable to said cutter member, said coupling rings comprising an internal ring for initial location within the bag, an external ring for initial location outside the bag and rib and groove arrangement for assisting a secure connection between the rings in one relative axial position, said internal ring and cutter member comprising a rib and groove arrangement for assisting a secure connection between the internal ring and cutter member in one relative axial position.

2. The apparatus of claim 1 wherein said internal coupling ring has a radially extending flange, said external coupling ring has a radially extending flange, said external ring has a diameter such that it snugly surrounds the diameter of the unflanged part of the internal ring, said cutter member has a diameter less than the internal diameter of the unflanged part of the internal ring.

3. The apparatus of claim 1 wherein said cutter member comprises a cylindrical body having cutting teeth surrounding at least a portion of the periphery of a first end of said cutter and a flange extending radially outwardly from said body at the opposite end, said elastomeric member comprising a radially inwardly extending flange at one end for overlapping said radially outwardly extending flange of said cutter member to couple said elastomeric member to said cutter member, said external ring having a radially outwardly extending flange at one end which is adapted to be spaced apart from said radially outwardly extending flange and to engage or be in close proximity to said radially inwardly extending flange of said elastomeric member when said coupling ring, cutter member and elastomeric member are coupled together.

4. Apparatus according to claim 1 in which the elastomeric member is affixed to the cutter member.

5. Apparatus according to claim 1 in which the two coupling rings and the cutter member are differently colored.

6. Apparatus according to claim 1 in which the two coupling rings and the cutter member are differently colored.

7. Apparatus according to claim 1 in which the elastomeric member is stepped.

8. Apparatus according to claim 4 in which the elastomeric member is stepped.

9. A method of attaching a catheter to a bag which receives discharge from a patient which includes trapping a portion of the bag wall between internal and external coupling rings so as to form a stretched area of bag wall within the rings, pushing a cutter blade of hollow tubular form into the external coupling ring and through the bag wall, the cutter blade having attached thereto an elastomeric catheter gripping member of substantially conical shape, and then continuing to push the hollow blade into the internal coupling ring so that a peripheral detent on either the exterior of the blade or the interior of the internal coupling ring engages with a counterpart groove or channel on the interior of the internal coupling ring or the exterior of the hollow cylindrical blade as the case may be.

* * * * *